United States Patent [19]

Koch et al.

[11] Patent Number: 5,723,590
[45] Date of Patent: Mar. 3, 1998

[54] ACID-CLEAVABLE SURFACTANTS BASED ON ALKYLGLYCOSIDES

[75] Inventors: Herbert Koch, Dorsten; Wulf Ruback, Duelmen; Wolfgang Schroeder, Dorsten, all of Germany

[73] Assignee: Huels Aktiengesellschaft, Marl, Germany

[21] Appl. No.: 652,093

[22] Filed: May 23, 1996

[30] Foreign Application Priority Data

Jul. 8, 1995 [DE] Germany .................. 195 24 973.9

[51] Int. Cl.$^6$ .................. C07H 15/06; C07H 15/08; C11D 3/22
[52] U.S. Cl. .................. 536/4.1; 536/18.5; 536/18.6; 536/120; 510/108; 510/470
[58] Field of Search .................. 536/18.5, 18.6, 536/4.1, 120, 123.13; 510/470, 108

[56] References Cited

U.S. PATENT DOCUMENTS

| | | | |
|---|---|---|---|
| 4,834,903 | 5/1989 | Roth et al. | 510/470 |
| 5,104,585 | 4/1992 | Fabry et al. | 252/555 |
| 5,179,201 | 1/1993 | Oftring et al. | 536/4.1 |
| 5,223,642 | 6/1993 | Schönwälder | 562/524 |
| 5,374,716 | 12/1994 | Biermann et al. | 536/18.6 |
| 5,520,834 | 5/1996 | Kroner et al. | 252/89.1 |
| 5,525,263 | 6/1996 | Bimczok et al. | 252/551 |

*Primary Examiner*—John Kight
*Assistant Examiner*—Howard C. Lee
*Attorney, Agent, or Firm*—Oblon, Spivak, McClelland, Maier & Neustadt, P.C.

[57] ABSTRACT

The invention relates to compounds of formula (I) herein which are reaction products of alkylglycosides with aldehydes and/or diacetals of short-chain alcohols and aldehydes, the acetals obtained being alkoxylated. The invention further relates to a process for producing the above-mentioned compounds and to the use of these compounds for preparing surfactants, especially for industrial detergents and cleaners.

8 Claims, No Drawings

1

ACID-CLEAVABLE SURFACTANTS BASED ON ALKYLGLYCOSIDES

BACKGROUND OF THE INVENTION

1. Field of the Invention

The present invention relates to reaction products of alkylglycosides with aldehydes and/or diacetals of short-chain alcohols and aldehydes, the acetals obtained being alkoxylated. The invention further relates to a process for producing the above-mentioned compounds and to the use of these compounds for preparing surfactants, especially for industrial detergents and cleaners. The alkylglycoside surfactants according to the invention are alkali-stable, low-foaming, cleavable into biodegradable fragments and exhibit altogether good wetting of hard surfaces.

DISCUSSION OF THE BACKGROUND

With the relinquishment of solvents, especially chlorinated hydrocarbons, the use of which in dip-cleaning for degreasing was drastically curtailed in Germany by the Second Federal Pollution Control Act Regulations, there is now an increasing trend in many fields and many countries towards the use of aqueous, surfactant-containing systems. However, their lack of resistance to microbial attack is an urgent problem. At present, this problem is solved either by the addition/replenishment of appreciable amounts of bactericides or by using refractory or undegradable ingredients—primarily surfactants.

One approach to solving this problem is the use of cleavable surfactants which are initially biologically hard, i.e. non-biodegradable, in their use form and, after use, for example in metal baths or generally in the cleaning of hard surfaces, are converted into biodegradable fragments by simple operations. It is a further aim to cleave the surfactants to obtain an aqueous and an organic phase in such a way that the organic phase can be separated off together with the greasy dirt, thereby reducing the level of organic waste in the wastewater. In certain circumstances, it can even be of economic interest to work up the removed organic load and thereby recover substances of value ("rent a chemical").

The chemical concept for this envisages primarily branched surfactants having a pH-sensitive function as a predetermined breaking point. By changing the pH it is possible to cleave the surfactant into biodegradable fragments and at the same time achieve a phase separation into an organic phase with hydrophobic soil particles and lipophilic surfactant constituents and an aqueous phase. The principle of pH-sensitive surfactants has for years been the subject of various papers and patents.

Industrial Launderer (July 1990, pp. 41 f) and also the technical information leaflet relating to TRITON® RW-Surfactant (July 1982) describe breaking stable emulsions of oils and wastewater, which contain pH-sensitive surfactants, by addition of acids and separating off the oil phase. This process gives substantially oil-free wastewaters. The surfactants used are ethoxylation products of primary amines. Products of this kind are known for their good cleaning performance, but they are not biodegradable.

DE 42 27 894 describes a process for reducing organic constituents in wastewaters from industrial laundries by using various branched alkanolamine/amide ethoxylates. The pH-sensitive surfactants described therein are said to be notable for a high cleaning performance, good separation from the emulsions in the event of a pH change, and also good biodegradability. A disadvantage is the use of amine intermediates for synthesizing these compounds and the associated nitrosamine problem.

Jaeger et al., in JACS 111, 3001–3006, describe branched acetal surfactants prepared by reaction of long-chain fatty ketones with glycerol.

Sokolowski, Piasecki et al., Tenside, Surf., Det. 30 (1993), 417, describe cleavable surfactants having an acetal group as pH-sensitive function. The acetal group is notable for high stability in a basic medium, while a cleavage occurs in the acid pH range. The disadvantage of the compounds described there are the costly starting materials.

SUMMARY OF THE INVENTION

It is an object of the present invention to provide cleavable surfactants which are free of the above-described disadvantages and preferably made from starting materials which are readily available, inexpensive and based ideally on renewable raw materials.

Mother object of the invention is to provide cleavable surfactants having the following industrial cleaning property profile:

1. Low foam
2. Alkali stability
3. "Biological hardness" (i.e., non-biodegradability) in their use form.
4. Acid-cleavability into biodegradable substructures.
5. High cleaning performance, on hard surfaces in particular.

These and other objects is achieved according to the present invention by alkylglycoside-based acid-cleavable surfactants.

DETAILED DESCRIPTION OF THE PREFERED EMBODIMENTS

The present invention accordingly provides acid-cleavable alkylglycoside-based surfactants according to the general formula I

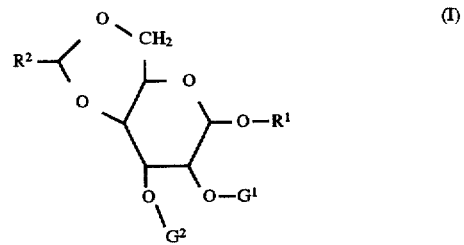

where $R^1$ represents unbranched or branched alkyl and/or alkylene groups having 1 to 20 carbon atoms, $R^2$ represents alkyl groups having 6 to 20 carbon atoms, $G^1$ represents $(EO)_v(PO)_wH$, $G^2$ represents $(EO)_x(PO)_yH$ where EO=ethyleneoxy ($—CH_2—CH_2—O—$) and PO=propyleneoxy ($—CH_2—CH_2—CH_2—O—$), and $v+w=0–30$, $x+y=0–30$; $v+w+x+y \geq 1$.

The invention further provides aqueous compositions containing at least one of the above compounds of formula I, a process for producing acid-cleavable surfactants, and a method of cleaning using acid-cleavable surfactants.

Unbranched or branched alkyl and alkenyl groups $R^1$ include for example methyl, ethyl, n-propyl, isopropyl, n-butyl, isobutyl, tert-butyl, n-pentyl, neopentyl, n-hexyl, n-heptyl, n-octyl, 2-ethylhexyl, n-nonyl, isononyl, n-decyl, isodecyl, n-undecyl, n-dodecyl, n-tridecyl, isotridecyl, n-tetradecyl, n-pentadecyl, n-hexadecyl, n-heptadecyl, n-octadecyl, n-eicosyl, oleyl, linolyl and linolenyl. The alkyl and alkenyl groups described herein can of course be mixtures. Preferably, $R^2$ comprises saturated and single or double-branched alkyl groups having 1–14 carbon atoms. Particular preference is given to methyl, butyl and also unbranched $C_8$–$C_{14}$-alkyl groups which are commercially available in the form of their glycosides.

Compounds of formula I can be produced using art-accepted methods by those of ordinary skill. Advantageously, the compounds of the formula I are prepared by reacting alkylglycosides with aldehydes or diacetals at temperatures of 50°–200° C. in a vacuum in the presence of catalytic amounts of acid. The products are cyclic acetals between the aldehyde carbon atom and the glycoside OH groups in positions 4 and 6 of the glycoside (see formula II). Another way of synthesizing the surfactant compounds of the formula I according to this invention consists in the transacetalization of fatty aldehyde diacetals of fatty aldehydes and short-chain alcohols with the corresponding alkylglycosides. This form of the reaction can be carried out under milder conditions than the direct acetalization.

Formula II

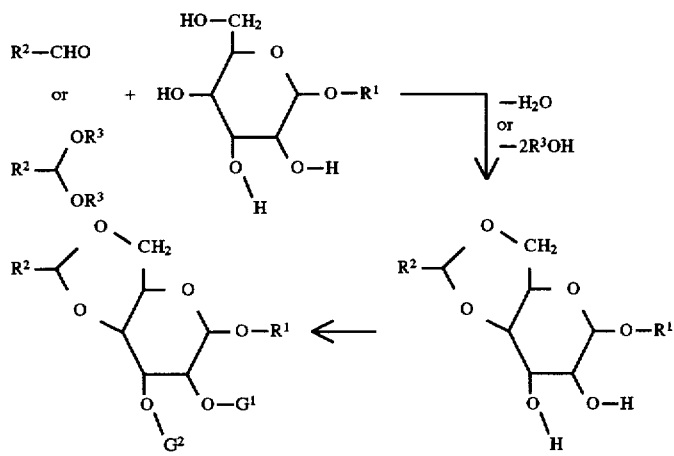

The aldehydes used are preferably those having a saturated $C_6$–$C_{20}$-alkyl chain. Examples are n-hexanal, n-heptanal, n-octanal, 2-ethylhexanal, n-nonanal, n-decanal, n-undecanal, n-dodecanal. Further representatives include all homologues having a branched $C_6$–$C_{20}$-carbon chain. These are obtainable for example by hydroformylation of olefins having an internal double bond. Since the olefins used here generally have a random homologue and isomer distribution, it is convenient to refer to an average number of carbon atoms in relation to the radicals $R^2$. $R^3$ comprises short (i.e., $C_1$–$C_{10}$), unbranched or branched alkyl groups, for example methyl, ethyl, propyl, butyl.

As well as direct acetalization, it is also possible, as described above, to carry out a transacetalization. For this purpose, the aldehydes are first converted with alcohols into the corresponding diacetals. Here it is customary to use shorter ($C_1$–$C_{10}$) alcohols, since the reaction is usually carried out in an excess of alcohol which has to be removed at the end by distillation. A further way of preparing dimethyl or diethyl acetals is the reaction of the aldehydes described with orthoesters (Houben-Weyl, Vol. 7, 4th Edition, pp. 417 ff.). These acetalization techniques are well known in the art.

The acetalization of the aldehydes, or the transacetalization of the aldehyde diacetals, with the alkylglycosides described can be carried out in the absence of a solvent. An additional inert solvent or diluent is normally not necessary, but can be added if needed, for example in the event of viscosity problems.

Suitable catalysts include mineral acids such as, for example, HCl, $H_2SO_4$, $H_3PO_4$ or $HClO_4$; organic carboxylic and sulphonic acids, for example methanesulphonic acid, p-toluenesulphonic acid, oxalic acid, formic acid, acetic acid, propionic acid, or Lewis acids such as, for example, $BF_3$, $AlCl_3$, $ZnCl_2$ or $TiCl_4$. The milder transacetalization may also be carried out using acidic clay minerals, for example K10. It is particularly advantageous to use p-toluenesulphonic acid as catalyst. The acidic catalyst is added in the amounts customary here, i.e. normally in an amount of about 0.1–5 mol %, based on the aldehyde component. A neutralization of the acidic catalyst after the reaction has taken place can be carried out with inorganic bases, for example NaOH, KOH, $K_2CO_3$, $Na_2CO_3$, or organic bases, for example trimethylamine, triethylamine, dimethylcyclohexylamine or pyridine. In principle, a separate neutralization is not necessary, since, in the subsequent operation, the alkoxylation of the basic structure is carried out under base catalysis. The course of the acetalization/transacetalization can be monitored and quantified from the amounts of water/alcohol distillate obtained.

The products obtained may contain certain amounts of higher oligomers, i.e. oligoglycosides, as secondary constituents.

The compounds are subsequently alkoxylated. The reaction is carried out with ethylene oxide and/or propylene oxide (EO/PO) in a conventional manner. Such synthesis is within the skill of the ordinary artisan. $G^1$ and $G^2$ can be random mixtures of EO/PO or a group composed of up to three uniform blocks of these alkylene groups.

The degrees of alkoxylation are between>0 and 30, preferably 5 and 20. The values of v+w and x+y are customarily averages.

The pH-sensitive surfactants of the formula I are generally useful as surface-active substances for industrial purposes and have a multiplicity of technical application possibilities. Of particular note is their use in cleaning baths of the metal industry for degreasing metal parts and also in the industrial cleaning of glass bottles, i.e. in particular in automatic cleaning processes. These purposes require surfactants which withstand the highly alkaline conditions of the cleaning baths, which are low-foaming and which ensure good wetting of hard surfaces.

The concentration of the acid-cleavable surfactants may be, for example, from 0.1 to 70% by weight, based on the preparation.

Setting the pH of an aqueous solution of the invention surfactants to a range of 0.5–6 will cleave the surfactants described herein in formula I and cause them to lose their surface-active character, as a result of which formed soil emulsions break and form two phases.

The invention will now be further described by reference to several non-limiting Examples.

PREPARATION EXAMPLES

Example 1

490 g (2.5 mol) of methyl-α-D-glucopyranoside and 575 g (2.5 mol) of lauraldehyde dimethyl acetal were initially charged to a 2 l three-neck flask under a protective gas. Following addition of 1.0 g of p-toluenesulphonic acid, the reaction batch was gradually heated to temperatures of 60°–90° C. and the methanol formed was collected. To ensure a uniform production of methanol and thus a uniform reaction, a vacuum was applied and gradually reduced down to 20 mbar, according to the amount of distillate collected. After 3–6 hours the theoretical amount of methanol had been collected. After transfer to an autoclave, the reaction product was admixed with 0.1–0.2% by weight of sodium hydroxide and carefully dewatered. This is followed by a reaction with ethylene oxide (about 1100 g=about 10 mol of EO/mol of starting material) at temperatures of 90°–140° C. After the desired amount of ethylene oxide had been taken up, the reaction batch was allowed to cool down, neutralized with lactic acid and finally filtered hot.

Example 2

293 g (0.31 mol) of a butanolic butylglycoside solution (28% strength) and 57 g (0.31 mol) of lauraldehyde solution were initially charged to a 2 l three-neck flask under a protective gas. Following addition of 1.8 g of p-toluenesulphonic acid, the reaction batch was gradually heated to temperatures of 60°–90° C. and the water of reaction formed was collected as an azeotrope with butanol under a vacuum of 250-20 mbar. After the theoretical amount of water had been eliminated, the residual butanol was condensed and the reaction product was transferred to an autoclave. Following addition of 0.1–0.2% by weight of sodium hydroxide, the batch was carefully dewatered. This was followed by reaction with ethylene oxide similarly to Example 1 using about 10 mol of EO/mol of starting material.

APPLICATION PROPERTIES

Foaming capacity and foam stability were determined in accordance with DIN 53902 in tap water (TW) at 20°–60° C. using aqueous mixtures having an active content of 0.1 g/l. The vessel (cylindrical shape, capacity 1000 ml) was in each case made up to a volume of 200 ml. The foam heights were read off after 60 beats and a subsequent standing time of 30 and 300 seconds.

The results (see table) reveal that, according to the foam test, the in-test compounds are all to be classed as very weak foamers.

The wetting capacity was determined in line with DIN-ISO 8022. In each case concentrations of 1.0 g of active content/l of tap water were investigated at 20° and 60° C., and the reported values are each averages of 10 measurements.

For the determination of the contact angle on PP reference is made to "Seifen-Öle-Fette-Wachse—Vol. 108—No. 15/1982".

TABLE

| | Foam test Foam heights (in ml) | | | | Wetting test Sink time | | Contact angle decrease on PP in DM water (in %) | | |
|---|---|---|---|---|---|---|---|---|---|
| | at ° C. | | at 60° C. | | (sec) in TW | | Conc. | Conc. | Conc. |
| Compound | 30 sec | 300 sec | 30 sec | 300 sec | 20° C. | 60° C. | 0.1 g/l | 1.0 g/l | 10 g/l |
| Ex. 1 | 60 | 50 | 20 | 10 | >300 | 85 | 20 | 46 | 48 |
| Ex. 2 | 50 | 40 | 10 | 0 | 59 | 49 | 21 | 35 | 41 |

This application is based on German application 195 24 973.9 filed Jul. 8, 1995, incorporated herein by reference.

What is claimed as new and is desired to be secured by letters patent of the United States is:

1. A compound according to formula I:

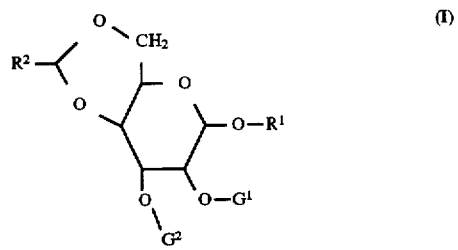

wherein $R^1$ represents unbranched or branched alkyl or alkylene group having 1 to 20 carbon atoms, $R^2$ represents alkyl group having 6 to 20 carbon atoms, $G^1$ represents $(EO)_v(PO)_wH$, $G^2$ represents $(EO)_x(PO)_yH$, EO is ethyleneoxy and PO is propyleneoxy, and v+w=0–30, x+y=0–30; v+w+x+y≧1.

2. The compound according to claim 1, wherein $R^1$ is an alkyl group having 1–14 carbon atoms.

3. The compound of claim 1, wherein $G^1$ and $G^2$ are ethylene oxide units.

4. The compound of claim 1, wherein v+x=5 to 20 and w=y=0.

5. A composition comprising water and at least one compound as described in claim 1.

6. A process for producing the compound of claim 1, wherein an alkylglycoside is acetalized/transacetalized with an aldehyde or a diacetal of an aldehyde and $C_1$–$C_{10}$ alcohol at temperatures of 50°–200° C. in the presence of catalytic amounts of acid and then alkoxylated with ethylene oxide and/or propylene oxide in the presence of a catalyst.

7. A method of cleaning comprising applying the compound of claim 1 to a surface in need of cleaning followed by removing said compound.

8. The composition according to claim 5, comprising 0.1 to 70% by weight based on the total weight of the composition, of said compound as described in claim 1.

* * * * *